US00PP21855P2

(12) United States Plant Patent van Veen

(10) Patent No.: US PP21,855 P2

(45) Date of Patent: Apr. 5, 2011

(54) *ASTILBE* PLANT NAMED 'LITTLE VISION IN PURPLE'

(50) Latin Name: ***Astilbe chinensis*×*Astilbe arendsii***
Varietal Denomination: Little Vision in Purple

(75) Inventor: Wilhelmus Franciscus van Veen, Noorden (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/653,764

(22) Filed: Dec. 16, 2009

(51) Int. Cl.
*A01H 5/00* (2006.01)

(52) U.S. Cl. ..... Plt./407

(58) Field of Classification Search ..... Plt./407
See application file for complete search history.

*Primary Examiner* — June Hwu

(74) *Attorney, Agent, or Firm* — C. A. Whealy

(57) ABSTRACT

A new and distinct cultivar of *Astilbe* plant named 'Little Vision in Purple', characterized by its compact, upright and strong plant habit; strong, healthy and dark-colored foliage; freely and uniformly flowering habit with inflorescences positioned above the foliar plane; deep pink-colored flowers; and good garden performance.

2 Drawing Sheets

Botanical designation: *Astilbe chinensis*×*Astilbe arendsii.*
Cultivar denomination: 'LITTLE VISION IN PURPLE'.

BACKGROUND OF THE INVENTION

The present invention relates to a new and distinct cultivar of *Astilbe* plant, botanically known as *Astilbe chinensis*× *Astilbe arendsii* and hereinafter referred to by the name 'Little Vision in Purple'.

The new *Astilbe* plant is a product of a planned breeding program conducted by the Inventor in Noorden, The Netherlands. The objective of the breeding program was to create new compact and strong *Astilbe* plants with attractive foliage and flower coloration.

The new *Astilbe* plant originated from a cross-pollination made by the Inventor in 2004 in Noorden, The Netherlands, of *Astilbe chinensis* 'Vision', not patented, as the female, or seed, parent with *Astilbe arendsii* 'Spartan', not patented, as the male, or pollen, parent. The new *Astilbe* plant was discovered and selected by the Inventor as a single flowering plant within the progeny of the stated cross-pollination in a controlled greenhouse environment in Noorden, The Netherlands in 2006.

Asexual reproduction of the new *Astilbe* plant by divisions in a controlled environment in Noorden, The Netherlands since January, 2007, has shown that the unique features of this new *Astilbe* plant are stable and reproduced true to type in successive generations.

SUMMARY OF THE INVENTION

Plants of the new *Astilbe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Little Vision in Purple'. These characteristics in combination distinguish 'Little Vision in Purple' as a new and distinct cultivar of *Astilbe:*

1. Compact, upright and strong plant habit.
2. Strong, healthy and dark-colored foliage.
3. Freely and uniformly flowering habit with inflorescences positioned above the foliar plane.
4. Deep pink-colored flowers.
5. Good garden performance.

Plants of the new *Astilbe* differ primarily from plants of the female parent. 'Vision', in the following characteristics:

1. Plants of the new *Astilbe* are more compact than plants of 'Vision'.
2. Leaves of plants of the new *Astilbe* are finer and stronger than leaves of plants of 'Vision'.
3. Plants of the new *Astilbe* have darker-colored flowers than plants of 'Vision'.

Plants of the new *Astilbe* differ primarily from plants of the male parent, 'Spartan', in the following characteristics:

1. Plants of the new *Astilbe* are more compact than plants of 'Spartan'.
2. Plants of the new *Astilbe* and 'Spartan' differ in flower color.

Plants of the new *Astilbe* can be compared to plants of *Astilbe chinensis* 'Pumila', not patented. In side-by-side comparisons conducted in Noorden, The Netherlands, plants of the new *Astilbe* differed from plants of 'Pumila' in the following characteristics:

1. Plants of the new *Astilbe* had stronger stems than plants of 'Pumila'.
2. Leaves of plants of the new *Astilbe* were darker in color and stronger than leaves of plants of 'Pumila'.

BRIEF DESCRIPTION OF THE PHOTOGRAPHS

The accompanying colored photographs illustrate the overall appearance of the new *Astilbe* plant, showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Little Vision in Purple' grown in a container.

The photograph at the top of the second sheet is a close-up view of typical inflorescences of 'Little Vision in Purple'.

The photograph at the bottom of the second sheet is a close-up view of the upper surface of a typical leaf of 'Little Vision in Purple'.

DETAILED BOTANICAL DESCRIPTION

The aforementioned photographs and following observations, measurements and values describe plants grown in containers in an outdoor nursery in Noorden, The Netherlands, under commercial practice during the summer. During the production of the plants, day temperatures ranging from 12° C. to 30° C. and night temperatures ranging from 5° C. to15° C. Plants were one year old when the photographs and description were taken. In the following description, color references are made to The Royal Horticultural Society Colour Chart, 2007 Edition, except where general terms of ordinary dictionary significance are used.

Botanical classification: *Astilbe chinensis*×*Astilbe arendsii* 'Little Vision in Purple'.

Parentage:

*Female, or seed, parent.*—*Astilbe chinensis* 'Vision', not patented.

*Male, or pollen, parent.*—*Astilbe arendsii* 'Spartan', not patented.

Propagation:

*Type.*—By divisions.

*Time to initiate roots.*—About 20 days at 15° C. to 18° C.

*Time to produce a rooted young plant.*—About two months at 18° C. to 20° C.

*Root description.*—Fine, fibrous; brown in color.

*Rooting habit.*—Freely branching; moderately dense.

Plant description:

*Plant form/habit.*—Herbaceous perennial; compact, upright and strong plant habit; roughly narrowly triangular; flowering stems and leaves basal; dense and bushy growth habit; low to moderate vigor; freely and uniformly flowering with numerous flowers on branched panicles positioned above the foliar plane.

*Growth rate.*—Moderate to slow; from divisions, about 20 weeks are required to produce fully-grown flowering plants.

*Plant height* (*soil level to top of foliar plane*).—About 11.1 cm.

*Plant height* (*soil level to top of inflorescences*).—About 38.9 cm.

*Plant width* (*spread*).—About 25.2 cm.

*Stem description.*—Length: About 8.4 cm. Diameter: About 5 mm. Internode length: About 4.2 cm. Strength: Strong. Texture: Densely pubescent. Color: Close to 146B.

Foliage description:

*Arrangement.*—Alternate; biternately compound.

*Leaf length* (*excluding petiole*).—About 14.3 cm.

*Leaf width.*—About 13.3 cm.

*Lateral leaflet length.*—About 3.8 cm.

*Lateral leaflet width.*—About 2.3 cm.

*Terminal leaflet length.*—About 4.3 cm.

*Terminal leaflet width.*—About 2.7 cm.

*Lateral and terminal leaflet shape.*—Ovate.

*Lateral and terminal leaflet apex.*—Acute.

*Lateral and terminal leaflet base.*—Rounded to attenuate.

*Lateral and terminal leaflet margin.*—Biserrate.

*Lateral and terminal leaflet texture, upper and lower surfaces.*—Sparsely pubescence, rough.

*Lateral and terminal leaflet venation pattern.*—Pinnate.

*Lateral and terminal leaflet color.*—Developing leaves, upper surface: Close to 144A to 144B. Developing leaves, upper surface: Close to 145A.

*Fully expanded leaves, upper surface.*—Darker than between 137A and 147A; venation, close to 147C. Fully expanded leaves, lower surface: Close to 147B; venation, close to 148D.

*Leaf petiole length.*—About 4.6 cm.

*Leaf petiole diameter.*—About 2 mm.

*Leaflet petiole length.*—About 8 mm.

*Leaflet petiole width.*—About 2 mm.

*Leaf and leaflet petiole texture, upper and lower surfaces.*—Smooth, glabrous.

*Leaf and leaflet petiole color, upper surface.*—Close to 146B; at the nodes, flushed with close to between 187A and 200B.

*Leaf and leaflet petiole color, lower surface.*—Close to 146B.

Flower description:

*Flower type/habit.*—Numerous single rotate flowers arranged on terminal branched panicles; flowers fact upright, outward or downward depending on position on the panicle; panicles narrowly triangular in shape; freely and uniformly flowering habit with about 12,500 flowers and flower buds per inflorescence.

*Fragrance.*—Faintly fragrant; sweet.

*Natural flowering season.*—Continuously flowering during the summer to late summer in The Netherlands.

*Postproduction longevity.*—Flowers last about ten days on the plant; flowers persistent.

*Flower buds.*—Height: About 2 mm. Diameter: About 1.5 mm. Shape: Broadly elliptical. Color: Close to 53C; towards the apex, tinged with close to 72B.

*Inflorescence height.*—About 28.9 cm.

*Inflorescence diameter.*—About 13.9 cm.

*Flower diameter.*—About 6 mm.

*Flower depth.*—About 4 mm.

*Petals.*—Quantity per flower: Typically five in a single whorl. Length: About 4 mm. Lobe width: About 1 mm. Shape: Narrowly oblanceolate. Apex: Broadly acute. Margin: Entire. Texture, upper and lower surfaces: Smooth, glabrous. Color: Developing petals, upper and lower surfaces: Close to N74C. Fully expanded petals, upper and lower surfaces: Close to 75A to 75B; color becoming closer to 76B to 76C with development.

*Sepals.*—Quantity per flower: Typically five in a single whorl, fused towards the base; campanulate calyx. Length: About 2 mm. Width: About 1 mm. Shape: Broadly ovate. Apex: Acute. Base: Cuneate, fused. Margin: Entire. Texture, upper and lower surfaces: Smooth, glabrous. Color: Developing sepals, upper and lower surfaces: Close to 53C. Fully developed sepals, upper surface: Close to 155A; towards the apex, close to 54A; towards the apical margins, close to 72D. Fully developed sepals, lower surface: Close to 54A; towards the apex and margins, close to 72D.

*Peduncles.*—Length: About 28.5 cm. Diameter: About 3 mm. Angle: Erect. Strength: Strong. Texture: Smooth, glabrous. Color: Close to 144C.

*Pedicels.*—Length: About 1 mm. Diameter: About 0.5 mm. Angle: About 45° from vertical. Strength: Moderately strong. Texture: Smooth, glabrous. Color: Close to 145C flushed with close to 54A.

*Reproductive organs.*—Stamens: Quantity per flower: Typically ten; anthers basifixed. Filament length: About 2 mm. Anther shape: Ovate. Anther length: About 0.5 mm. Anther color: Close to 158B to 158C. Pollen amount: Scarce. Pollen color: Close to 155D. Pistils: Quantity per flower: Two. Pistil length: About 2.5 mm. Style length: About 2 mm. Style color: Between 67D and 68B. Stigma shape: Club-shaped. Stigma color: Close to 67B to 67C. Ovary color: Close to 68B.

*Seed/fruit.*—Seed and fruit development have not been observed.

Disease/pest resistance: Plants of the new *Astilbe* have not been noted to be resistant to pathogens and pests common to *Astilbe.*

Garden performance: Plants of the new *Astilbe* have been observed to have good garden performance and tolerate rain, wind and high temperatures of about 35° C.; plants of the new *Astilbe* have been observed to be hardy to USDA Zone 5.

It is claimed:

1. A new and distinct *Astilbe* plant named 'Little Vision in Purple' as illustrated and described.

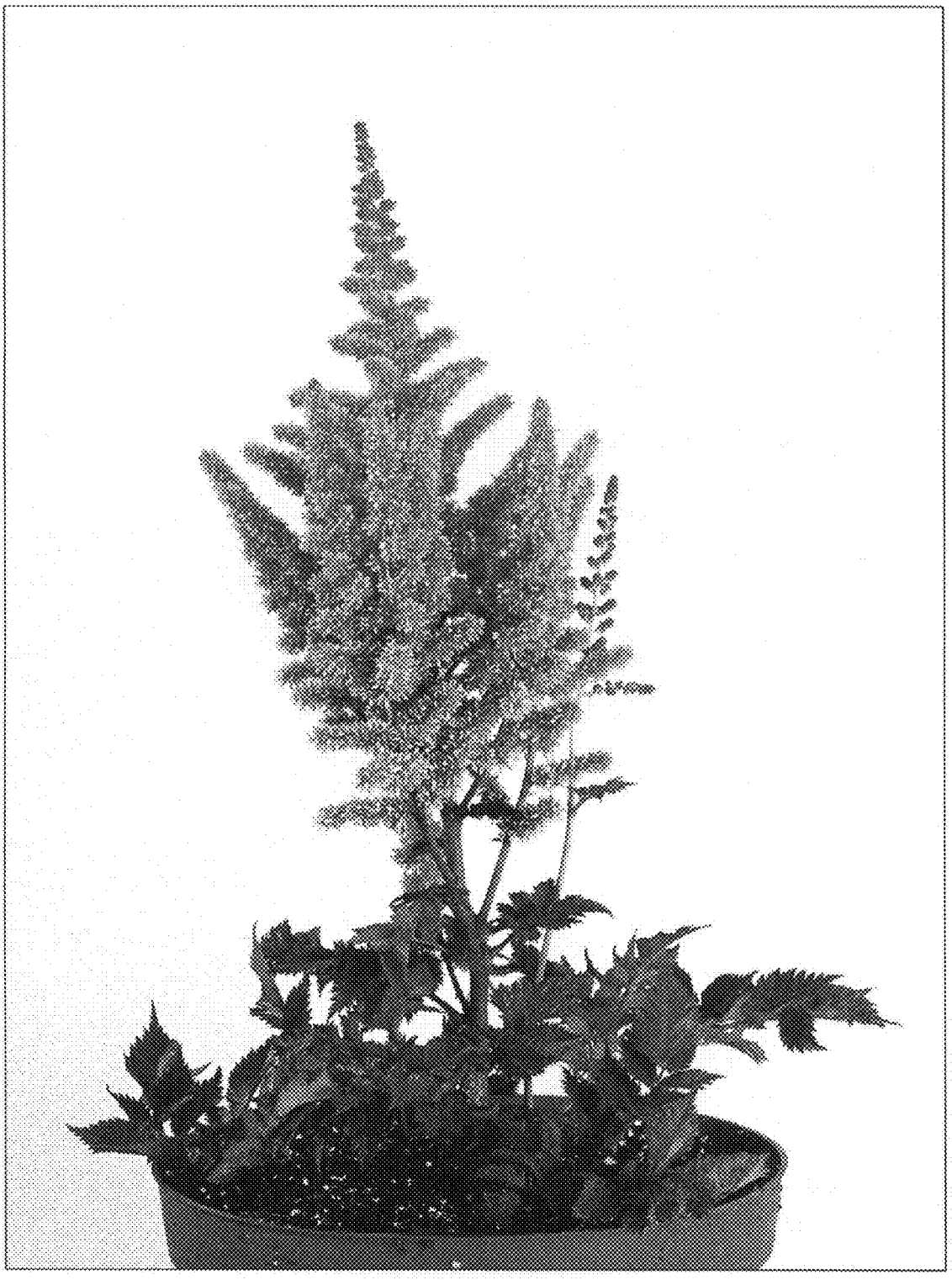

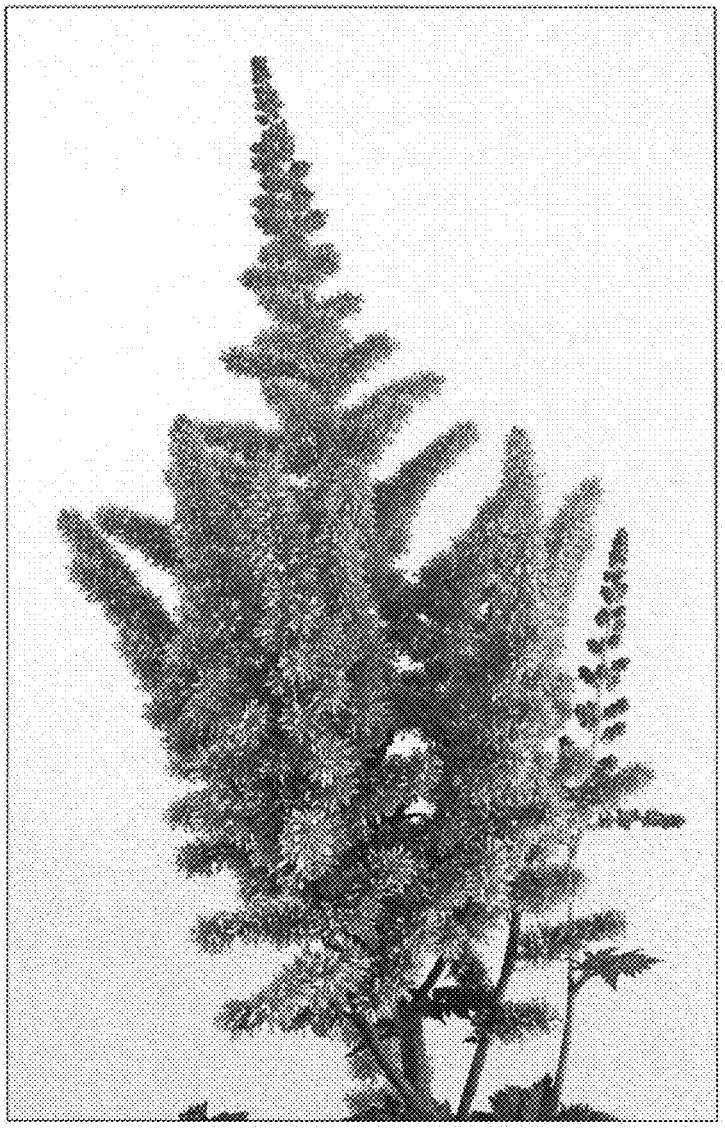
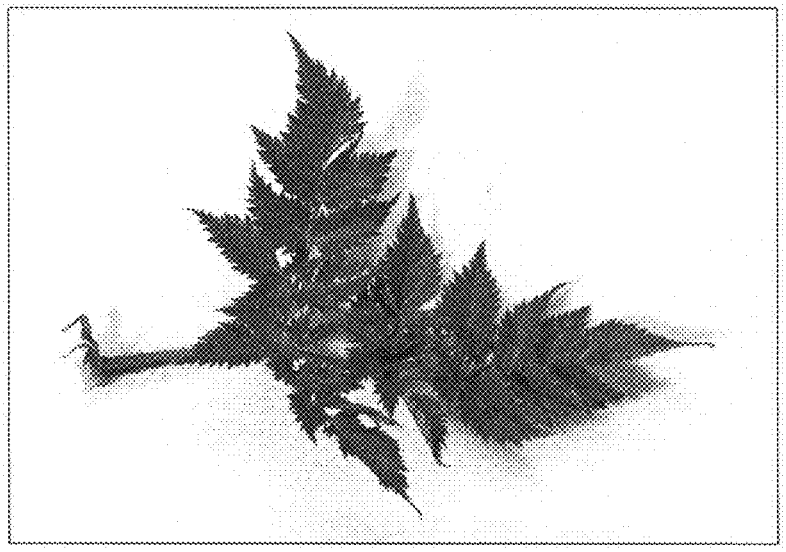

* * * * *